United States Patent [19]
Blomquist

[11] Patent Number: 5,876,370
[45] Date of Patent: Mar. 2, 1999

[54] INTERMITTENT FLUID DELIVERY APPARATUS AND METHOD

[75] Inventor: Michael L. Blomquist, Coon Rapids, Minn.

[73] Assignee: SIMS Deltec, Inc., St. Paul, Minn.

[21] Appl. No.: 978,779

[22] Filed: Nov. 26, 1997

Related U.S. Application Data

[63] Continuation of Ser. No. 540,960, Oct. 11, 1995, abandoned.

[51] Int. Cl.$^6$ .................................................. A61M 31/00
[52] U.S. Cl. .............................. 604/65; 604/67; 604/246; 604/151; 128/DIG. 12; 128/DIG. 13; 417/12
[58] Field of Search ................................. 604/65–7, 151, 604/245–6; 128/DIG. 12, DIG. 13; 417/12

[56] References Cited

U.S. PATENT DOCUMENTS

| | | | |
|---|---|---|---|
| 4,320,757 | 3/1982 | Whitney et al. | 128/214 F |
| 4,624,661 | 11/1986 | Arimond | 604/151 |
| 4,676,776 | 6/1987 | Howson | 604/31 |
| 4,785,799 | 11/1988 | Schoon et al. | 128/53 |
| 5,000,739 | 3/1991 | Kulisz et al. | 604/246 X |
| 5,010,473 | 4/1991 | Jacobs | 364/150 |
| 5,174,472 | 12/1992 | Raque et al. | 417/12 X |
| 5,181,910 | 1/1993 | Scanlon | 604/67 |
| 5,221,268 | 6/1993 | Barton et al. | 604/246 X |
| 5,256,157 | 10/1993 | Samiotes et al. | 604/246 |
| 5,389,078 | 2/1995 | Zalesky et al. | 604/151 |
| 5,616,121 | 4/1997 | McKay | 604/35 |

FOREIGN PATENT DOCUMENTS

| | | |
|---|---|---|
| 2060151 | 8/1992 | Canada . |
| 0 188 288 | 7/1986 | European Pat. Off. . |

OTHER PUBLICATIONS

*Provider® One Instruction Manual*, Pancretec, Inc. (undated).

*CADD–Micro™ Ambulatory Infusion Pump, Model 5900 Operator's Manual*, Pharmacia Deltec (Oct. 1993).

Operator's manual for a CADD–Micro™ Ambulatory Infusion Pump Model 5900, front cover and pp. ii–vi and 1–84, copyright 1993.

Operator's manual for a CADD–PLUS® Ambulatory Infusion Pump Model 5400, two front cover pages, pp. iii–vi, pp. 1–55, and two back cover pages, copyright 1990.

*Primary Examiner*—Wynn Wood Coggins
*Assistant Examiner*—Jennifer R Sadula
*Attorney, Agent, or Firm*—Merchant, Gould, Smith, Edell, Welter & Schmidt, P.A.

[57] ABSTRACT

An apparatus and method for delivering a fluid during a series of infusion intervals, consecutive infusion intervals being separated by a non-infusion interval, each infusion interval beginning at a predetermined time and having a first predetermined period, and each non-infusion interval beginning at a predetermined time and having a second predetermined period. The apparatus comprises a pump mechanism and circuitry operatively connected to the pump mechanism. The circuitry is configured so that, if the pump is disabled during one of the infusion intervals, the circuitry will determine the length of time the pump is disabled, interrupt the infusion interval while the pump is disabled, and delay the beginning of subsequent infusion and non-infusion intervals for a length of time approximately equal to the length of time the pump is disabled. If the pump is disabled and then enabled during the second predetermined period of one of the non-infusion intervals, begin the succeeding infusion interval at the predetermined beginning time.

8 Claims, 6 Drawing Sheets

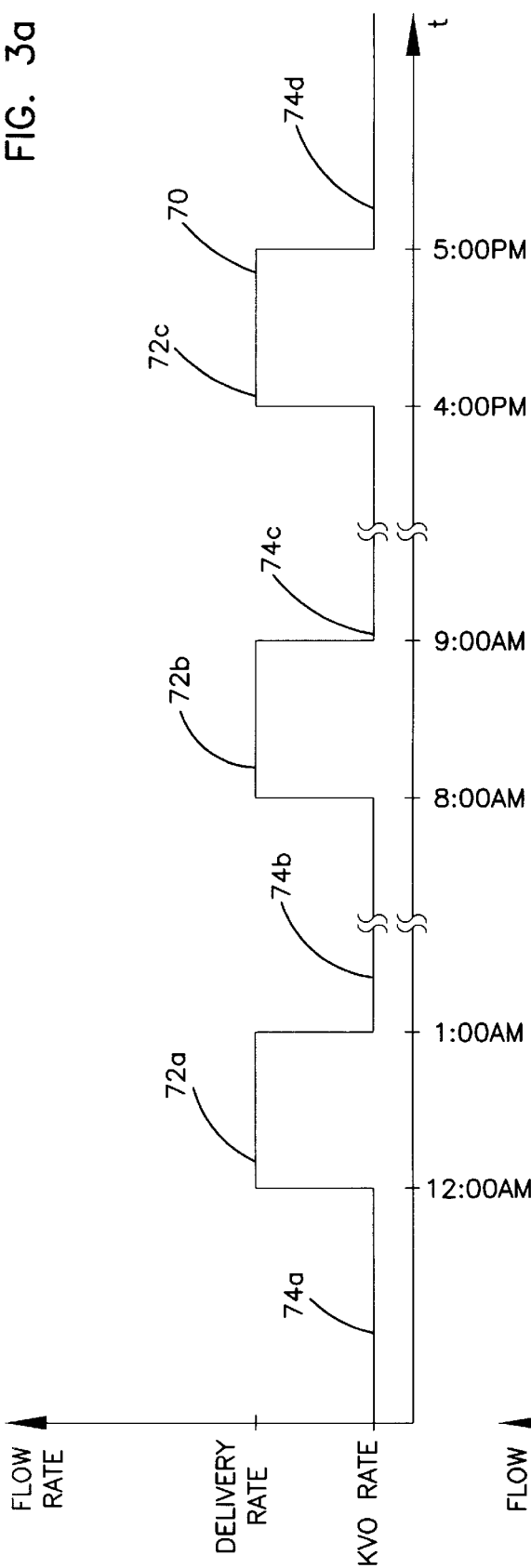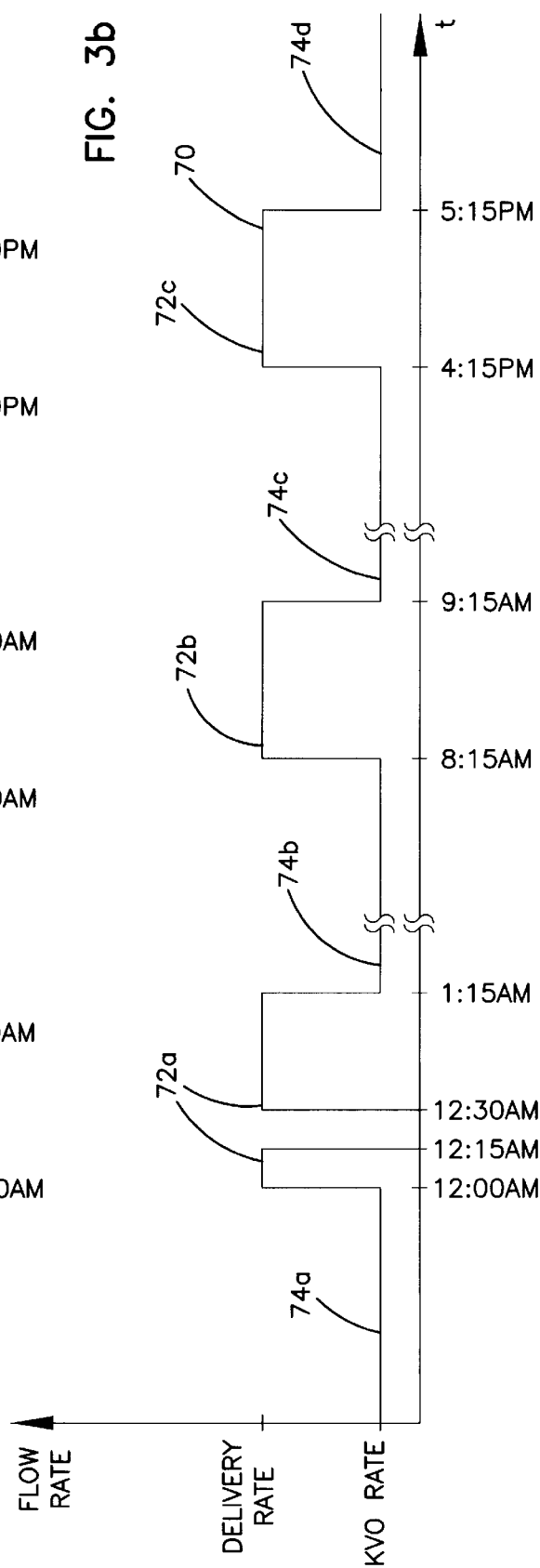

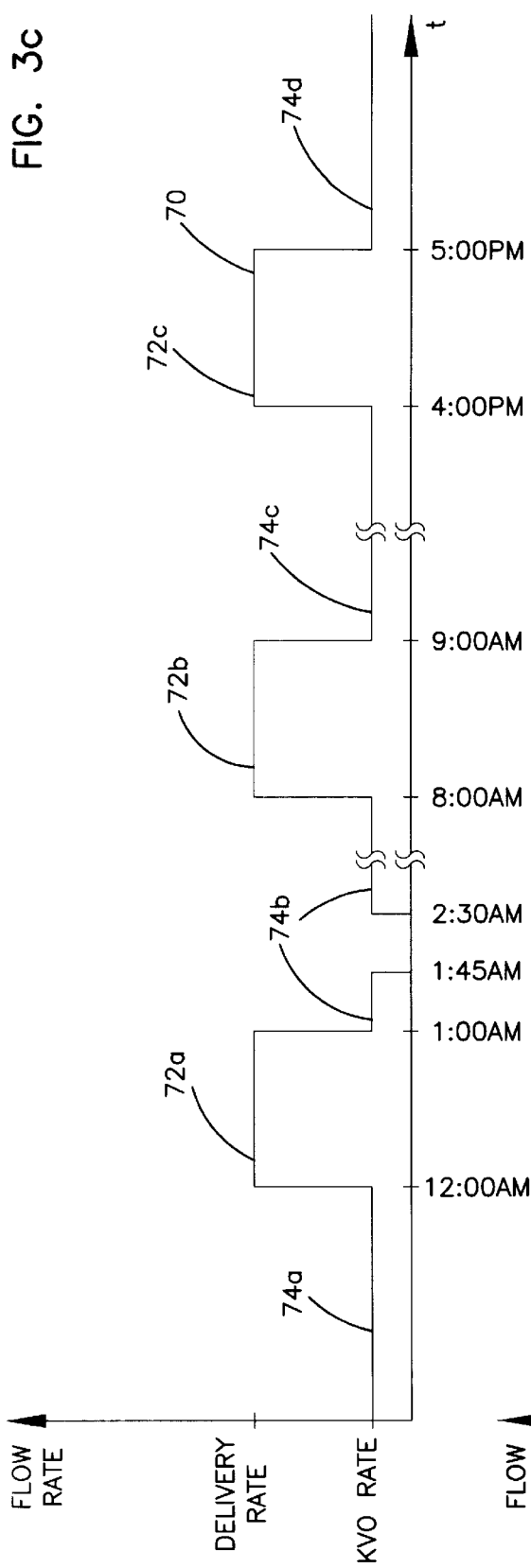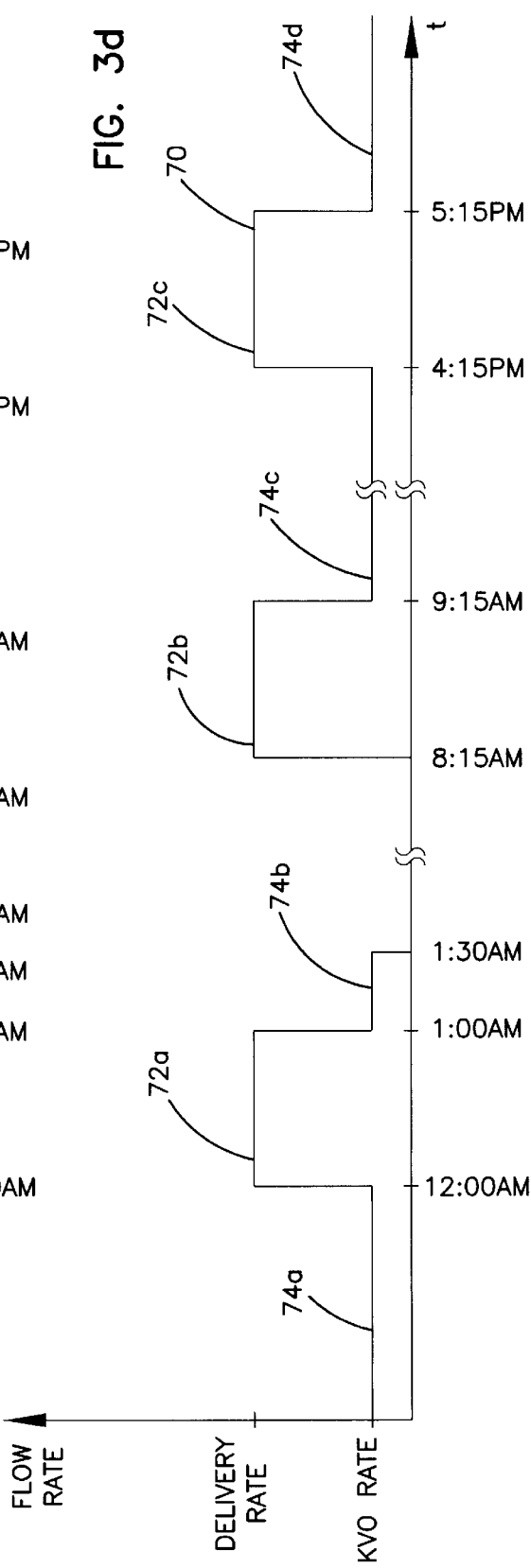

INTERMITTENT FLUID DELIVERY APPARATUS AND METHOD

This is a file wrapper Continuation of application Ser. No. 08/540,960, filed Oct. 11, 1995, now abandoned.

TECHNICAL FIELD

The present invention relates to an apparatus and method for infusing a prescribed fluid into a patient, and more particularly to an infusion pump that is capable of intermittent fluid delivery.

BACKGROUND

When treating a patient, it is often beneficial to intermittently infuse fluids such as drugs and nutrients. This type of delivery is useful in a variety of treatments, including chemotherapy, pain control, nutritional therapies, antibiotic treatments, and other types of medical treatments. An example of intermittent delivery might call for delivering 25 milliliters of an antibiotic during a one-hour interval and then repeating the delivery every 8 hours. The interval during which the fluid is delivered is called an infusion interval. The interval between consecutive infusion intervals is called a non-infusion interval.

Additionally, there is often a need to disable the pump from time to time in order to allow the patient to move more freely for activities such as exercise or showers. The pump also may have to be disabled for maintenance such as changing the fluid reservoir or power supply.

As a result, there is a need for a medical pump and method that permits a patient to get a full dose of fluid despite disabling the pump. There is also a need for a pump that will provide a predictable window of time during which the patient or caregiver can disable the pump without delaying subsequent infusion intervals or non-infusion intervals.

SUMMARY

The present invention relates to an apparatus for delivering a fluid during a series of infusion intervals. Consecutive infusion intervals are separated by a non-infusion interval. Each infusion interval begins at a predetermined time and has a first predetermined period, and each non-infusion interval begins at a predetermined time and has a second predetermined period. The apparatus comprises a pump mechanism and circuitry operatively connected to the pump mechanism. The circuitry is configured so that if the pump is disabled during one of the infusion intervals, the circuitry will determine the length of time the pump is disabled, interrupt the infusion interval while the pump is disabled, and delay the beginning of subsequent infusion and non-infusion intervals for a length of time approximately equal to the suspension in fluid delivery. If the pump is disabled and then enabled during the second predetermined period of one of the non-infusion intervals, the pump will begin the succeeding infusion interval at the predetermined beginning time.

The present invention also relates to a method of delivering a fluid with a pump during a series of infusion intervals. Consecutive infusion intervals are separated by a non-infusion interval. Each infusion interval begins at a predetermined time and has a first predetermined period, and each non-infusion interval begins at a predetermined time and has a second predetermined period. The method comprises the step of delivering the fluid during each infusion interval. The method comprises the additional steps of, if the pump is disabled during one of the infusion intervals, determining the length of time the pump is disabled, interrupting the infusion interval while the pump is disabled, and delaying the beginning of subsequent infusion and non-infusion intervals for a length of time approximately equal to the delay in fluid delivery. The method also comprises the step of, if the pump is disabled and then enabled during the second predetermined period of one of the non-infusion intervals, beginning the succeeding infusion interval at the predetermined beginning time.

DESCRIPTION OF THE DRAWINGS

FIGS. 3a–3d set forth diagrams that represent the flow rate of fluid versus time during intermittent delivery.

DETAILED DESCRIPTION

Figure 1:
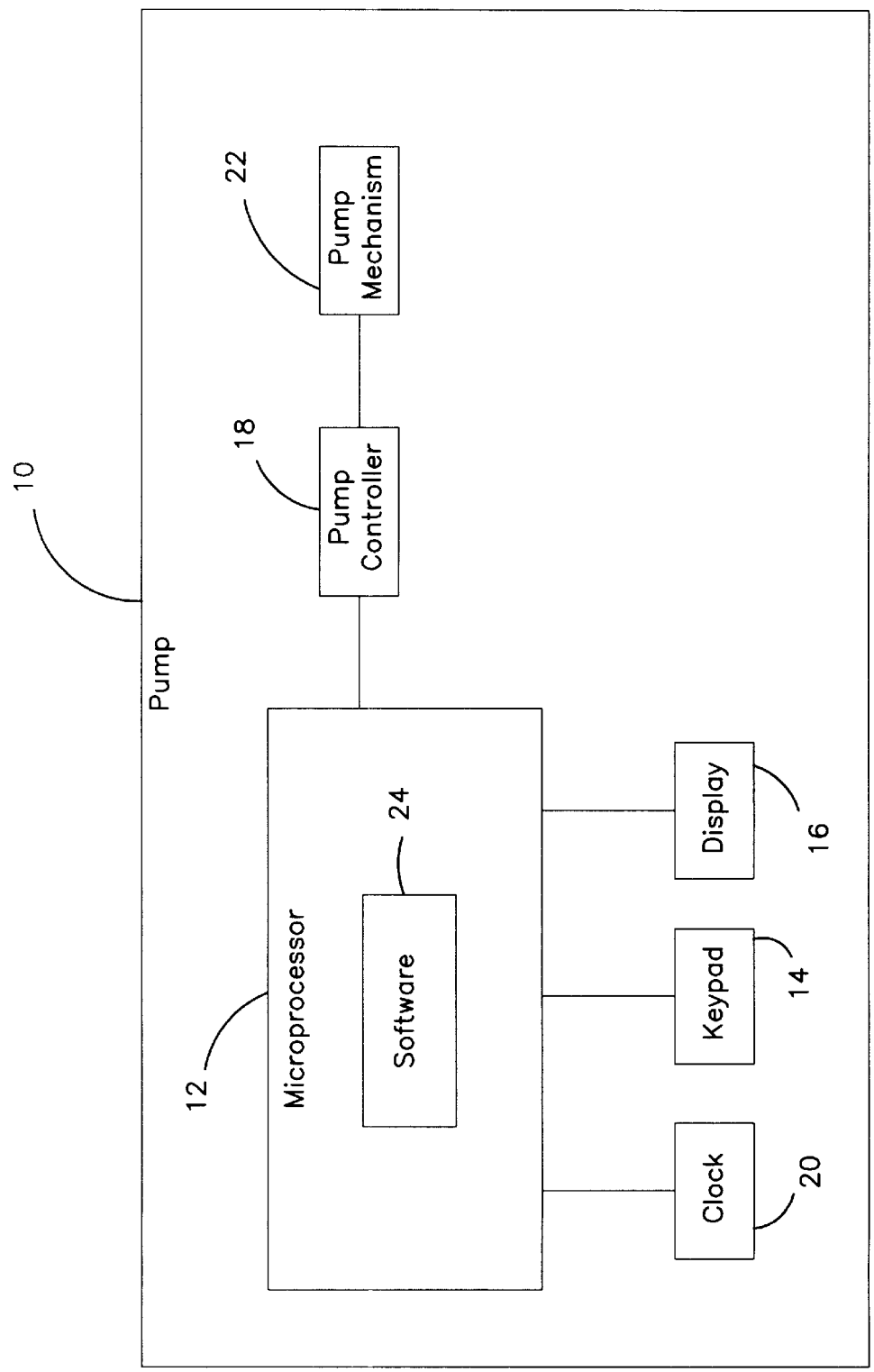
FIG. 1 is a functional block diagram of a pump that embodies the present invention.

A preferred embodiment of the present invention will be described in detail with reference to the drawings, wherein like reference numerals represent like parts, elements, and assemblies throughout the several views. Reference to the preferred embodiment does not limit the scope of the invention, which is limited only by the scope of the claims attached hereto.

In general terms the present invention is directed to a pump for infusing fluid into a patient. The pump is configured to infuse fluid according to a predetermined schedule or delivery cycle. The delivery schedule consists of a series of infusion intervals during which the pump infuses a therapeutic level of fluid into the patient. Consecutive infusion intervals are separated by a non-infusion interval during which the pump either infuses no fluid or a non-therapeutic level of fluid sufficient to keep the venous access open, which is called delivering a KVO rate. Each infusion interval has a first predetermined period and each non-infusion interval has a second predetermined period.

If the pump is disabled during one of the infusion intervals, the circuitry will determine the length of time the pump is disabled. The infusion interval is then interrupted while the pump is disabled, and the beginning of subsequent infusion interval and non-infusion intervals is delayed for a length of time approximately equal to the length of time the pump is disabled. In other words, the infusion interval will resume and be completed when the pump is enabled again, and the predetermined beginning time of the subsequent infusion intervals and non-infusion intervals are reset.

If the pump is disabled and then enabled during the second predetermined period of one of the non-infusion intervals, the succeeding infusion interval begins at its predetermined beginning time. In other words, the non-infusion interval is not suspended or interrupted while the pump is disabled, and the predetermined beginning time of the subsequent infusion interval is not reset or delayed.

An embodiment of the present invention will now be described in more detail. Referring to FIG. 1, the present invention can be implemented using a pump 10 that includes a pump mechanism that is controlled by circuitry. In more specificity, the pump 10 includes a microprocessor 12, which is linked to a keypad 14, a display 16, a pump controller 18, a clock 20, and sensors (not shown). The sensors can be configured to determine whether the pump 10 has malfunctioned or to automate other pump functions.

The pump controller 18 is linked to a pump mechanism 22. The pump mechanism 22 is configured to infuse fluid into a patient. Infusing fluid can be accomplished by placing the pump mechanism in fluid communication with a venous access in a patient (not shown). The fluid is pumped from a reservoir (not shown). Such a pump is described in more detail in U.S. Pat. Nos. 5,338,157 and 5,364,242, the disclosures of which are hereby incorporated by reference.

The pump 10 is powered by a primary power supply (not shown). Additionally, there is a backup battery (not shown) in case there is a failure of the primary power supply. The backup battery provides power to the microprocessor 12, display 16, and clock 20. One skilled in the art will realize that the backup battery could provide backup power to other components of the pump 10.

The keypad 14 includes a start/stop key (not shown). Activating the start/stop key signals the microprocessor 12, which then toggles the pump 10 between an enabled state and a disabled state. A user might activate the start/stop key to disable the pump 10 for a variety of activities such as changing batteries, resupplying or replacing the fluid reservoir, and disconnecting the pump 10. There are many reasons that a patient might disconnect the pump 10 including exercising and taking a shower.

Activating the start/stop key will manually toggle the pump 10 between an enabled state and a disabled state. One skilled in the art will realize that the pump 10 also becomes disabled when fluid flow is suspended during one of the infusion intervals or when delivery of the KVO rate becomes suspended during one of the non-infusion intervals. Thus, the pump 10 becomes disabled when there is an event such as a dry fluid reservoir, a failure of the pump mechanism, a power failure, a blockage of the venous access, or any other type of failure associated with the pump 10.

The clock 20 is implemented using a real-time clock integrated circuit (IC), which provides a real-time basis for measuring time. A possible IC that can be used for the clock 20 is chip no. DP8572A, which is manufactured by National Semiconductor. Because the backup battery provides a secondary source of power for the clock 20, it can continue to keep track of time if there is a failure of the primary power supply.

One skilled in the art will realize that there are other ways to implement the clock 20. For example, the clock 20 could be implemented using a 1-second oscillator (not shown). In this configuration, the microprocessor 12 would count the number pulses emitted by the oscillator and use this information to calculate the time. However, the backup battery would need to provide power to both the oscillator and the microprocessor 12 if there is a failure of the primary power supply.

The microprocessor 12 executes and operates according to software 24. Under control of the software 24, the pump 10 can deliver a prescribed dose of fluid to the patient according to an intermittent delivery schedule. The intermittent delivery schedule sets forth predetermined times of the day for the beginning of the infusion intervals and the beginning of the non-infusion intervals.

The infusion interval is the period during which the pump delivers fluid to the patient at a predetermined delivery rate. The non-infusion interval is the period between consecutive infusion intervals. During the non-infusion interval, the pump can either deliver no fluid or deliver a non-therapeutic level of fluid that is sufficient to keep the venous access from becoming clogged. As discussed above, delivering a non-therapeutic level of fluid to keep the venous access open is called delivering a KVO rate.

The same fluid is typically delivered during the infusion interval and the non-infusion interval. Alternatively, the pump 10 can be configured as a 2-channel pump so that during the non-infusion intervals, the pump 10 will deliver a second type of fluid that will have minimal harmful effects.

Figure 2A:
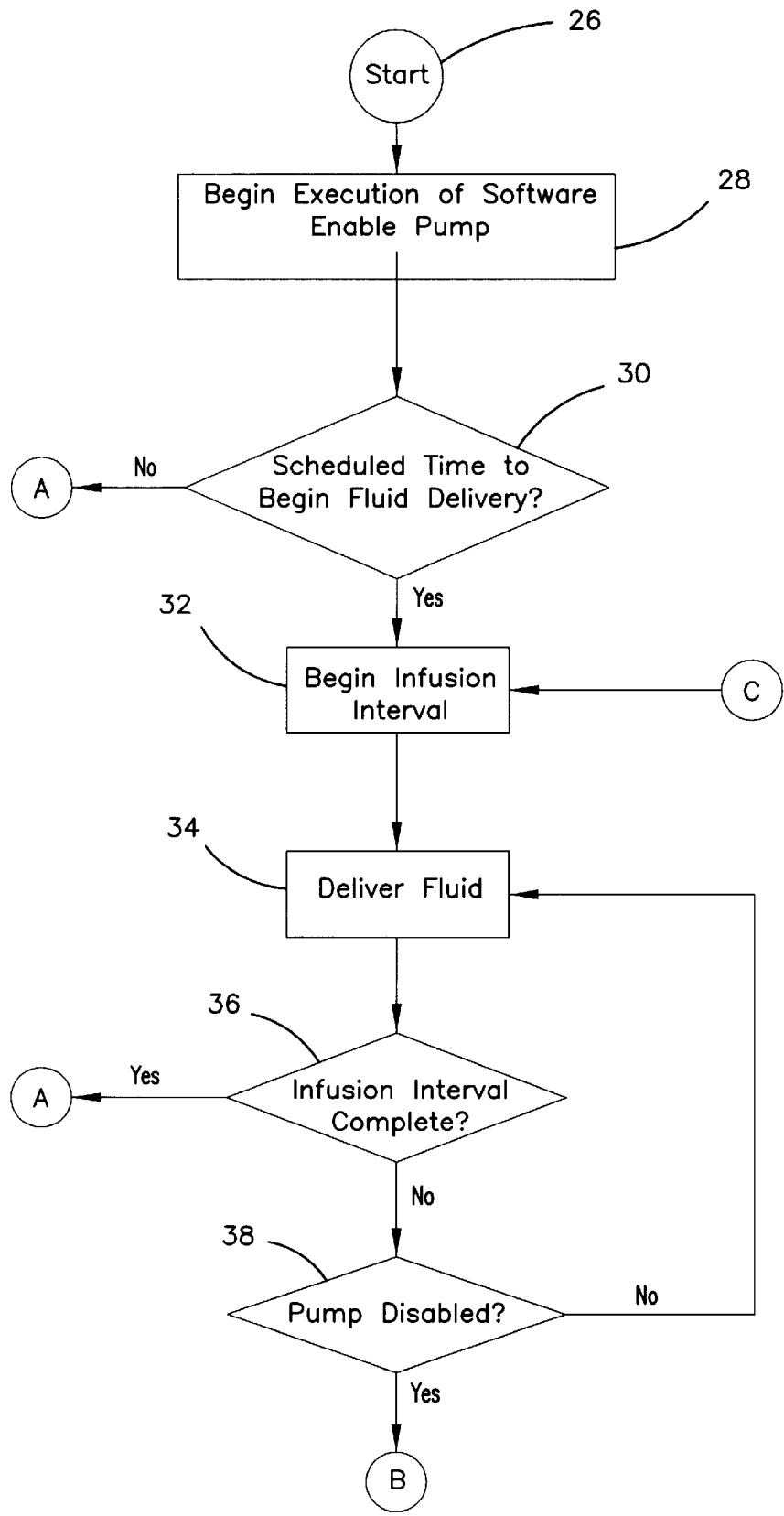
FIGS. 2a–2c set forth a flow-chart that represents the sequence of events that occur when the pump shown in FIG. 1 is disabled and then re-enabled.
Figure 2B:
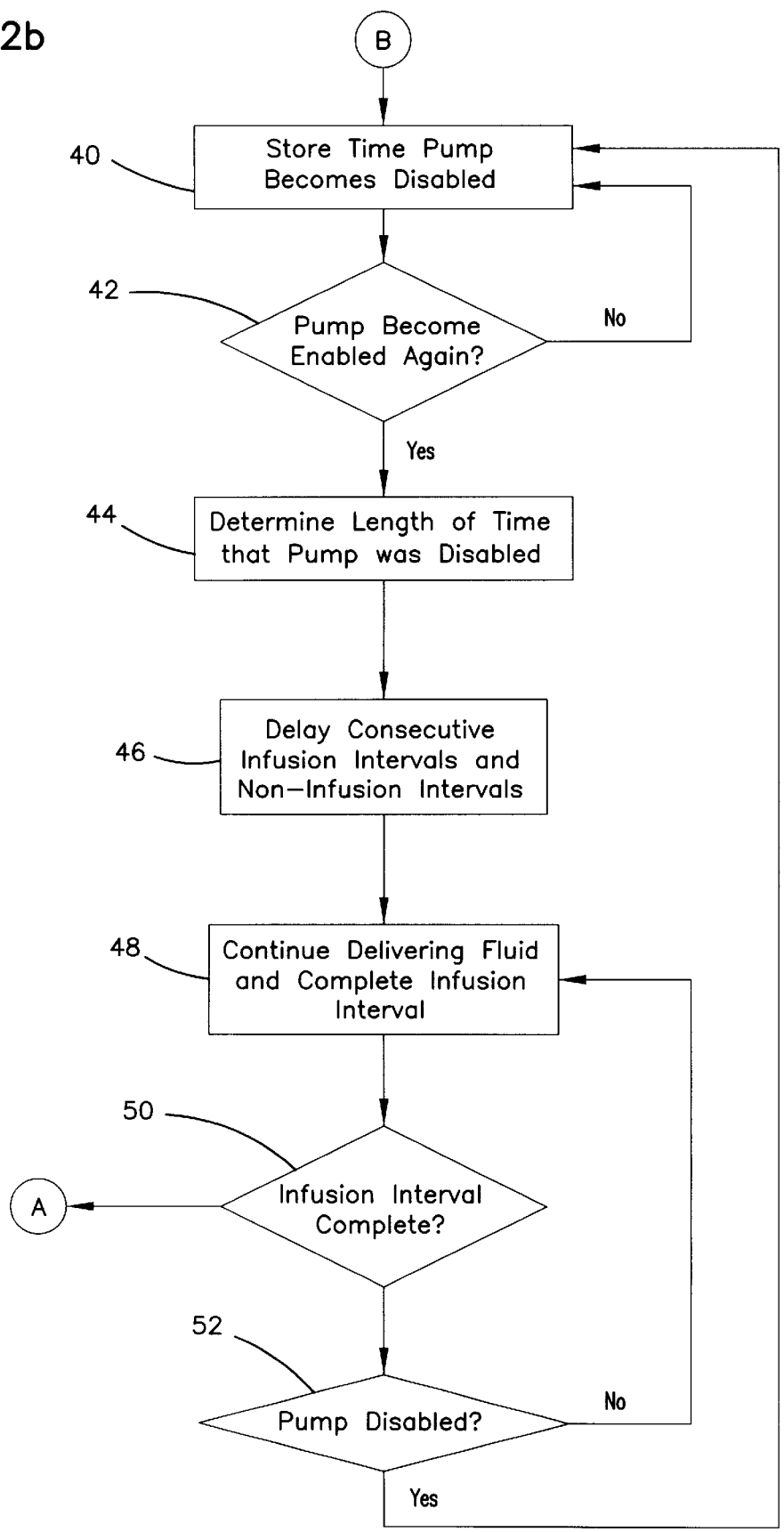
Figure 2C:
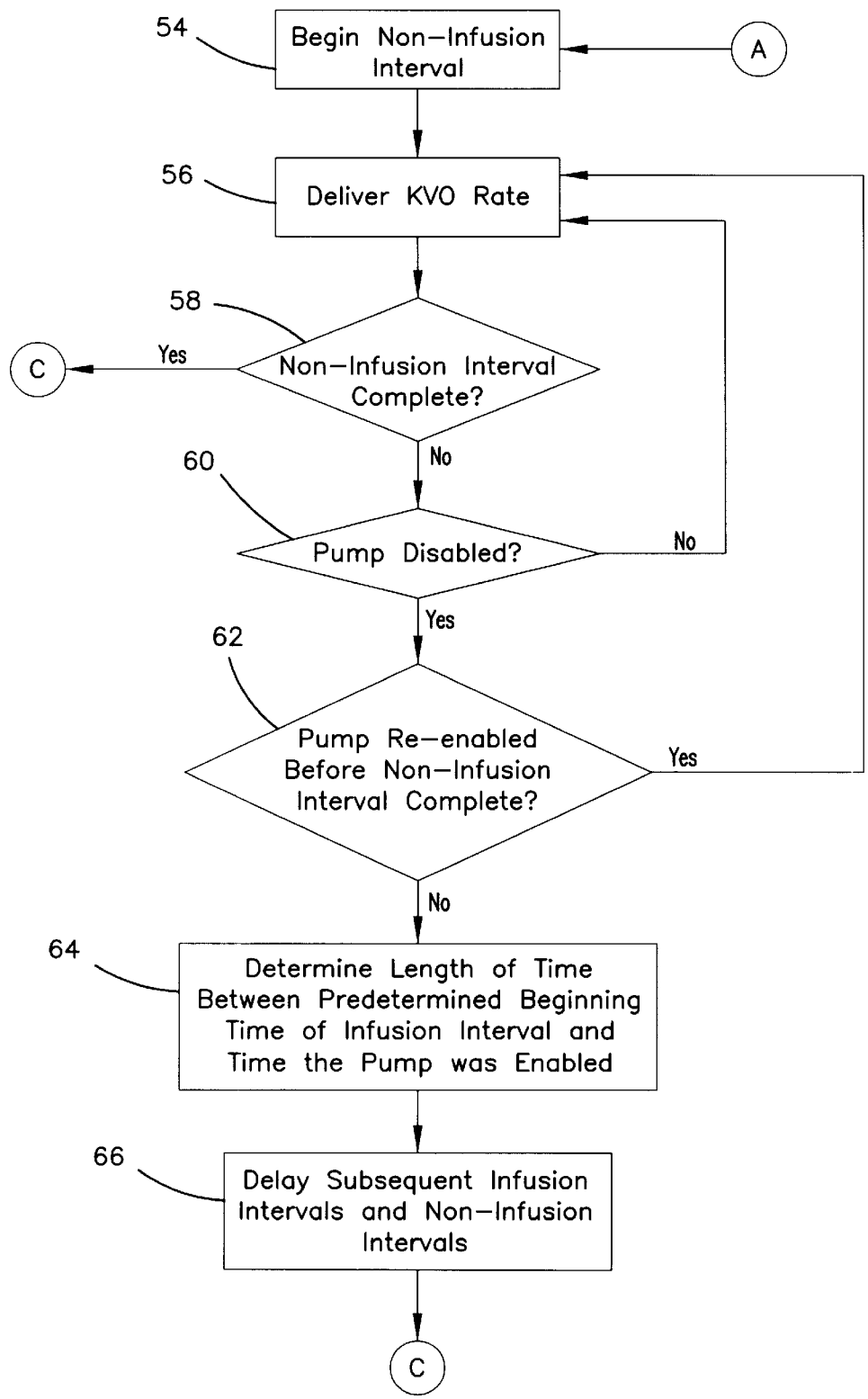

The flow chart set forth in FIGS. 2a–2c represents the sequential operation of an intermittent fluid delivery pump that embodies the present invention. The sequential operation of the pump 10 begins when the microprocessor 12 starts to execute the software 24 and the pump 10 is initially enabled (blocks 26 and 28).

The microprocessor 12 monitors the clock 20 in order to determine the current time. The microprocessor 12 then compares the current time to the predetermined beginning time of the first infusion interval. When the microprocessor 12 determines that the current time corresponds to the predetermined beginning time of the first infusion interval (block 30), the microprocessor 12 will begin an infusion interval (block 32) and instruct the pump controller 18 and hence the pump mechanism 22 to deliver fluid at the predetermined delivery rate (block 34).

When the time indicated by the clock 20 corresponds to the predetermined beginning time for the next non-infusion interval (block 36), which indicates that the current infusion interval is complete, the microprocessor 12 will instruct the pump controller 18 either to deactivate the pump mechanism 22 so that no fluid is delivered or to reduce the delivery rate so that the fluid is delivered at only a KVO rate.

If the pump becomes disabled during the infusion interval (block 38) the microprocessor 12 will store the time that the pump 10 becomes disabled (block 40) and interrupt the infusion interval. If the pump 10 becomes enabled again so that fluid delivery resumes (block 42), the microprocessor 12 will store the time at which the pump 10 becomes enabled and calculate the length of time that the pump 10 was disabled (block 44). The microprocessor 12 will then delay the predetermined beginning times for subsequent infusion intervals and non-infusion intervals (block 46). The delay is approximately equal to the length of time that the pump 10 was disabled. In other words, the microprocessor 12 will reset the predetermined beginning times for subsequent infusion intervals and non-infusion intervals.

When the pump 10 becomes enabled again, the microprocessor 12 will resume and complete the current infusion interval (block 48) and cause the pump controller 18 and pump mechanism 22 to continue pumping fluid until the prescribed dose is complete. When the infusion interval is complete (block 50), the pump 10 will begin a non-infusion interval (block 54). If the pump 10 is repeatedly deactivated before the infusion interval is complete (block 52), the microprocessor 12 will cause the pump 10 to repeat the sequence of events set forth in blocks 40, 42, 44, 46, 48, and 50.

During the non-infusion interval, the microprocessor 12 instructs the pump controller 18 and hence the pump mechanism 22 to deliver fluid at the KVO rate (block 56). The microprocessor 12 also continues to monitor the clock 20 and compares the current time to the predetermined beginning time set for the next infusion interval. If the time as determined by the clock 20 matches the predetermined time set for the beginning of the next infusion interval (block 58), the microprocessor 12 will begin the next infusion interval (block 32) and instruct the pump controller 18 and hence the pump mechanism 22 to begin delivering fluid at the predetermined delivery rate (block 34).

If the pump 10 becomes disabled before the non-infusion interval is complete (blocks 60), the microprocessor 12 will continue to monitor the clock 20. If the pump 10 is then enabled before the predetermined beginning time set for the next infusion interval (block 62), the pump mechanism 22 will continue to deliver fluid at the KVO rate (block 56) until the predetermined beginning time of the next infusion interval (block 58). The predetermined beginning time for the next infusion interval is not rescheduled or delayed.

If the pump 10 is re-enabled after the predetermined time the corresponds to the beginning of the succeeding or next scheduled infusion interval, the microprocessor 12 will store the time at which the pump 10 becomes re-enabled. The microprocessor 12 will then calculate the length of time between re-enablement of the pump 10 and the predetermined time that corresponds to the beginning time of the succeeding infusion interval (block 64). The microprocessor 12 will delay the predetermined beginning times for subsequent infusion intervals and non-infusion intervals by an amount approximately equal to the delay between re-enablement of the pump 10 and the predetermined time that the infusion interval was scheduled to begin (block 66). The predetermined beginning times of subsequent infusion and non-infusion intervals are reset accordingly. The microprocessor 12 will then begin the next infusion interval (block 32) and cause the pump controller 18 and the pump mechanism 22 to deliver fluid at the predetermined delivery rate (block 34).

As shown in FIGS. 3a–3d, intermittent fluid delivery according to the present invention can be described using a series of charts that show the delivery rate of the prescribed fluid versus time. FIG. 3a represents a typical intermittent delivery schedule 70 having a plurality of infusion intervals 72a, 72b, and 72c and a plurality of non-infusion intervals 74a, 74b, 74c, and 74d. Each infusion interval 72a, 72b, and 72c begins at a predetermined time. The predetermined times are 12:00 a.m., 8:00 a.m., and 4:00 p.m., respectively. Each infusion interval 72a, 72b, and 72c has a duration of 1 hour so that the predetermined beginning times of the non-infusion intervals 74a, 74b, 74c, and 74d are 5:00 p.m., 1:00 a.m., 9:00 a.m., and 5:00 p.m., respectively.

FIG. 3b shows the flow rate during intermittent delivery when the pump 10 becomes disabled during an infusion interval. In this example, the pump is disabled during infusion interval 72a for 15 minutes. The infusion interval 72a is completed when fluid delivery resumes so that the patient receives the prescribed dose of fluid. The predetermined beginning time of the subsequent infusion intervals 72b and 72c and the non-infusion intervals 74b, 74c, and 74d is then delayed for 15 minutes.

FIG. 3c shows the flow rate during intermittent delivery of a fluid when the pump 10 is disabled during a non-infusion interval and then re-enabled before the predetermined beginning time of the next infusion interval. In this example, the pump 10 is disabled for 15 minutes during non-infusion interval 74b. In this scenario, the subsequent infusion intervals 72b and 72c and the non-infusion intervals 74c and 74d are not delayed.

FIG. 3d shows the flow rate during intermittent fluid delivery when the pump is disabled during a non-infusion interval and re-enabled after the predetermined beginning of the succeeding or next scheduled infusion interval. In this example, the pump 10 is disabled during non-infusion interval 74b and re-enabled at 8:15 a.m., which is 15 minutes after the predetermined beginning time of infusion interval 72b. In this scenario, the infusion interval 72b begins when the pump 10 is re-enabled. The subsequent infusion interval 72c and the non-infusion intervals 74c and 74d are then delayed for 15 minutes.

The present invention has many significant advantages. One advantage is that the infusion intervals are not delayed if the pump is disabled during the non-infusion interval. As a result, the user knows with certainty when they can disable the pump without disrupting the intermittent delivery schedule. Another advantage is that the patient will still receive the prescribed dose of fluid if the pump does happen to become disabled during an infusion interval. This advantage is especially important when delivering fluids such as antibiotics where there could be serious adverse effects if the patient dose not receive the proper dose. Yet another advantage is that the pump will always maintain the proper interval between infusion intervals. As a result, consecutive infusion intervals will never occur back-to-back, which could cause harmful effects such as an overdose. This advantage is particularly important when delivering toxic drugs such as those used for chemotherapy.

These advantages make the present invention generally beneficial over other forms of fluid delivery such as real-time delivery and non-real time delivery. In real time delivery, the fluid delivery period would begin at a specific time of day. As an example, one type of treatment may call for three infusion intervals a day beginning at 12:00 a.m., 8:00 a.m., and 4:00 p.m. One difficulty arises if the pump would deliver the prescribed fluid only during the originally scheduled infusion interval. If the pump is then disabled during the originally scheduled infusion interval, delivery during the suspended portion of the infusion interval is lost. As a result, the patient would not receive the prescribed dose of fluid. This loss of delivery could have detrimental effects for certain types of treatments such as the delivery of antibiotics.

On the other hand, if the full delivery of the fluid is always made, suspending the infusion interval may result in either back-to-back infusion intervals or two consecutive infusion intervals that end and begin within a very short time frame. Such an event could cause an overdose or other harmful effects.

Non-real time delivery is another possible technique for delivering fluids. If a pump would be disabled during non-real time delivery, the corresponding interval or non-infusion interval is suspended. When the pump is then re-enabled, it would complete the suspended infusion interval or non-infusion interval, whichever the case may be. The start times of all the subsequent infusion and non-infusion intervals then would be delayed for a period approximately equal to the amount of time that the pump was disabled.

For an example of non-real time delivery, assume that a delivery protocol calls for three infusion intervals a day beginning at 12:00 a.m., 8:00 a.m., and 4:00 p.m. Further assume that each infusion interval has a length of one hour and the pump is disabled during one of the non-infusion intervals, say from 1:00 p.m. to 1:30 p.m. In this example, the last infusion interval for the day will begin at 4:30 p.m., not 4:00 p.m. as originally scheduled and as the patient might expect. The infusion intervals for the following days will then begin at 12:30 a.m., 8:30 a.m., and 4:30 p.m.

Delaying subsequent infusion intervals in this manner has significant shortcomings. If a pump needs to be disabled, it is preferable to do so during a non-infusion interval so that delivery of the fluid is not interrupted. However, disabling the pump during a non-infusion interval would delay both subsequent infusion intervals and subsequent non-infusion intervals. As a result, the intermittent delivery schedule would become disrupted and it can become difficult to schedule a time to disable the pump at a later time without interrupting fluid delivery during an infusion interval.

Another shortcoming arises when a pump is disabled during a non-infusion interval and remains disabled for a long period of time. For example, suppose a non-infusion interval would be scheduled to last for seven hours, but the pump becomes disabled and remains disabled for six hours. The gap between the infusion intervals will be thirteen hours—almost twice the originally scheduled length. Again, such a delay between infusion intervals could have serious consequences.

While the invention has been described in conjunction with a specific embodiment thereof, different alternatives, modifications, and variations will be apparent to those skilled in the art. Accordingly, the invention is not limited to the described embodiments or the use of elements having specific configurations and shapes as presented herein. Rather, the scope of the invention is limited only by the following claims.

The claimed invention is:

1. An apparatus for delivering a fluid during a series of infusion intervals, consecutive infusion intervals being separated by a non-infusion interval, each infusion interval beginning at a predetermined time and having a first predetermined period, and each non-infusion interval beginning at a predetermined time and having a second predetermined period, the apparatus comprising:

a pump mechanism; and circuitry operatively connected to the pump mechanism, the circuitry being configured so that:

if the pump is disabled during one of the infusion intervals, the circuitry will determine the length of time the pump is disabled, interrupt the infusion interval while the pump is disabled, and delay the beginning of subsequent infusion and non-infusion intervals for a length of time approximately equal to the length of time the pump is disabled; and if the pump is disabled and then enabled during the second predetermined period of one of the non-infusion intervals, begin the succeeding infusion interval at the predetermined beginning time.

2. The apparatus of claim 1 wherein the circuitry is further configured so that if the pump mechanism is disabled during one of the non-infusion intervals and is enabled after the predetermined time that corresponds to the beginning of the succeeding infusion interval, the circuitry will:

determine the length of delay between the predetermined time that corresponds to the beginning of the succeeding infusion interval and enablement of the pump mechanism;

restart the following infusion interval upon enablement of the pump mechanism; and delay the beginning of subsequent infusion and non-infusion intervals for a length of time approximately equal to the length of delay between the predetermined time that corresponds to the beginning of the succeeding infusion interval and enablement of the pump mechanism.

3. The apparatus of claim 1 wherein the patient has a venous access and the pump mechanism is configured to be placed in fluid communication with the venous access, further wherein the pump mechanism and circuitry are configured to cooperate in order to deliver a sufficient amount of fluid during the non-infusion period to keep the venous access open.

4. The apparatus of claim 3 wherein the sufficient amount of fluid during the non-infusion period to keep the venous access open is a non-therapeutic level of the fluid.

5. A method of delivering a fluid with a pump during a series of infusion intervals, consecutive infusion intervals being separated by a non-infusion interval, each infusion interval beginning at a predetermined time and having a first predetermined period, and each non-infusion interval beginning at a predetermined time and having a second predetermined period, the method comprising the steps of:

delivering the fluid during each infusion interval;

if the pump is disabled during one of the infusion intervals, determining the length of time the pump is disabled, interrupting the infusion interval while the pump is disabled, and delaying the beginning of subsequent infusion and non-infusion intervals for a length of time approximately equal to the length of time the pump was disabled; and if the pump is disabled and then enabled during the second predetermined period of one of the non-infusion intervals, beginning the succeeding infusion interval at the predetermined beginning time.

6. The method of claim 5 comprising the additional steps of:

if the pump mechanism is disabled during one of the non-infusion intervals and is enabled after the predetermined time that corresponds to the beginning of the succeeding infusion interval, determining the length of delay between the predetermined time that corresponds to the beginning of the succeeding infusion interval and enablement of the pump mechanism;

restarting the following infusion interval upon enablement of the pump mechanism; and delaying the beginning of subsequent infusion and non-infusion intervals for a length of time approximately equal to the length of delay between the predetermined time that corresponds to the beginning of the succeeding infusion interval and enablement of the pump mechanism.

7. The method of claim 5 wherein the patient has a venous access through which the fluid is delivered, the method comprising the additional step of delivering a sufficient amount of fluid during the non-infusion period to keep the venous access open.

8. The method of claim 7 wherein the step of delivering a sufficient amount of fluid during the non-infusion period comprises the step of delivering a non-therapeutic level of the fluid.

* * * * *